United States Patent [19]

Rosenthal et al.

[11] Patent Number: 4,882,127

[45] Date of Patent: Nov. 21, 1989

[54] DEVICE FOR SOLID PHASE SEQUENCING OF NUCLEIC ACID FRAGMENTS

[75] Inventors: Andre Rosenthal, Berlin; Hans-Dieter Hunger; Horst Kagelmaker, both of Zepernick; Monika Grätschus, Berlin, all of German Democratic Rep.

[73] Assignee: Akademie Der Wissenschaften Der DDR, Berlin, German Democratic Rep.

[21] Appl. No.: 120,092

[22] Filed: Nov. 12, 1987

Related U.S. Application Data

[62] Division of Ser. No. 761,107, Jul. 31, 1985, Pat. No. 4,849,077.

[30] Foreign Application Priority Data

Aug. 6, 1984 [DD] German Democratic Rep. .................... 2659974
Aug. 6, 1984 [DD] German Democratic Rep. .................... 2659982
May 14, 1985 [DD] German Democratic Rep. .................... 2763283

[51] Int. Cl.⁴ .................. C12M 1/16; B01L 3/00; B01L 9/00
[52] U.S. Cl. .................. 422/50; 422/65; 422/66; 422/73; 422/116; 422/102; 422/104; 422/131; 435/300; 435/301
[58] Field of Search .................. 435/300, 301, 809; 422/65, 66, 73, 116, 131, 50, 102, 104

[56] References Cited

U.S. PATENT DOCUMENTS

| | | | |
|---|---|---|---|
| 3,497,320 | 2/1970 | Blackburn et al. | 422/66 X |
| 3,770,380 | 11/1973 | Smith | 422/73 X |
| 3,888,113 | 6/1975 | Miraneda | 422/73 X |
| 4,058,370 | 11/1977 | Suovaniemi | 422/100 |
| 4,155,711 | 5/1979 | Zelagin et al. | 422/65 X |
| 4,341,735 | 7/1982 | Seifried | 422/66 |
| 4,349,510 | 9/1982 | Kolehmainen et al. | 422/66 |
| 4,446,104 | 5/1984 | Hämmerling et al. | 435/300 X |
| 4,568,520 | 2/1986 | Ackermann et al. | 422/101 X |

*Primary Examiner*—Carl D. Price
*Attorney, Agent, or Firm*—Michael J. Striker

[57] ABSTRACT

A device for solid phase sequencing of nucleic acid segments comprises a plurality of sequencing blocks for storing and processing n nucleic acid fragments immobilized on carrier segments or in homogenous phase during a sequencing process, each of a sample dosing device for immobilizing n labeled nucleic acid samples from the sequencing blocks onto areas of a carrier matrix in a simultaneous fashion and including a capillary holder and a plurality of capillaries corresponding to the number n of different nucleic acid samples to be sequences and arranged according to the distribution of the reaction vessels with a distance between capillary orifices from the capillary holder greater than a depth of the reaction vessels, a plurality of carrier holders for fixing carrier matrices in a predetermined position during the immobilization of the nucleic acid samples with the sample dosing device and each having a recess corresponding to respective dimensions of the carrier matrix and a plurality of bores with a number and distribution pattern corresponding to those of the reaction vessels and with a diameter which is somewhat larger than a diameter of the capillary, a punch for simultaneous punching of n immobilized and chemically modified nucleic acid samples as individual carrier segments out of the carrier matrix into the sequencing blocks and including a punching plate and a plurality of punching pins with a number and distribution pattern which also corresponds to those of the reaction vessels.

12 Claims, 4 Drawing Sheets

DEVICE FOR SOLID PHASE SEQUENCING OF NUCLEIC ACID FRAGMENTS

This is a division, of application Ser. No. 761,107, filed Jul. 31, 1985 now U.S. Pat. No. 4,849,077.

FIELD OF INVENTION

This invention relates to sequence analysis of nucleic acid fragments (DNA and RNA) in molecular biology and recombinant DNA technology as well as to sequence analysis of oligodeoxy- and oligoribonucleotides after chemical synthesis.

BACKGROUND OF THE INVENTION

A process for solid phase sequencing of nucleic acid fragments has been described (A. Rosenthal and H.-D. Hunger DD 228906; A. Rosenthal, S. Schwetner, V. Hahn and H.-D. Hunger (1985) Nucleic Acids Research 13 (1985) 1173-1184). This process allows a larger number of nucleic acid fragments to be simultaneously sequenced by solid phase chemical degradation using a novel carrier matrix and has the potential for automation. However, the number of fragments which can be effectively and simultaneously sequenced by this process using ordinary laboratory equipment (commercially available test tubes, ordinary laboratory glass equipment) is limited. In addition, there is the danger of confusing immobilized nucleic acid fragments during performance of the process. Devices for sequencing of nucleic acid fragments by solid phase chemical degradation are not known.

SUMMARY OF THE INVENTION

The object of the invention is a device for sequencing nucleic acid fragments by solid phase chemical degradation which allows simultaneous immobilization of n different nucleic acid fragments (1 n 1000) on a carrier matrix with a two-dimensional form, simultaneous chemical treatment of the immobilized nucleic acid fragments during nucleic acid modification reactions, simultaneous sorting the immobilized nucleic acid fragments by punching distinct areas of the carrier matrix with the immobilized nucleic acid fragments out of the carrier matrix into special sequencing blocks, simultaneous chemical treatment of the sorted carrier segments with the immobilized nucleic acid fragments during piperidine or aniline reaction as well as simultaneous treatments such as washings, centrifugations, high and low temperature treatments and lyophilizations.

In accordance with the present invention a device is provided made up of the following components: sequencing blocks with common lids, sample dosing system, holder for carrier matrix, and punching device.

The sequencing block consists of a square or cubical base block, whereby other shapes are allowed. Within the sequencing block n reaction vessels are embedded or inserted. The number of reaction vessels depends on the number of different nucleic acid fragments (samples) to be analyzed. The reaction vessels have a cylindrical and/or conical form and are individually inserted into the sequencing block or rigidly connected in a microtiter plate like manner (i.e. deep-drawn reaction vessels). The volume of each reaction vessel may vary between 30 ul and 2 ml. Each type of reaction vessel (individual test tubes or deep-drawn vessel system) can easily be inserted into the sequencing block and replaced at the end of the sequencing process. The sequencing block is made from such a material which exhibits efficient heat conducting properties and allows the reaction vessels to be easily heated to 90° C.

Each sequencing block is marked to fix its constellation to the other sequencing blocks as well as to other parts of the device which are required according to the inventive process operation.

Each sequencing block is additionally furnished with mechanical guides and thus can be combined unmistakably with the punching device.

Each sequencing block can be sealed with a special lid which is designed in such a way as to fit exactly onto the block thereby tightly closing each individually reaction vessel. It consists of a nondeformable rigid lid on which a yieldable packing is mounted which presses on the reaction vessels. The lid can be mounted onto the block by using special mounting elements.

Part of the device according to the present invention is a sample dosing device for the simultaneous application of n different nucleic acid fragments as labelled liquid samples onto the carrier matrix. The dosing device is provided with n equally long capillaries corresponding to the number of different samples to be processed. The number of different capillaries also correlates with the number of different reaction vessels being present in the sequencing block. The capillaries are inserted into a capillary holder and have the same distribution pattern as the reaction vessels, i.e. one capillary for each reaction vessel of the sequencing block. The inner diameter of a capillary may vary between 0.1 and 3 mm. Thus, the sample dosing device is capable to simultaneously transfer n different nucleic acid samples, whereby volumes are in the 0.5 to 5 ul range. By means of markings and guides the capillaries are always associated with the same samples (reaction vessels).

The punch according to the present invention assists the sample immobilisates to be punched out of the carrier matrix, and thereby to simultaneously transfer them into the reaction vessels of the sequencing block. It consists of a plate with inserted punching pins which have the same distribution pattern as the reaction vessels in the sequencing block. The punching device can be combined unmistakably with each sequencing block. Punching is performed after inserting the carrier matrix into a special holder which locks in on the sequencing block in a specified position. Depending on construction of the punching device the punched carrier segments may have diameters in the 0.5 and 5 mm range.

Sample dosing is performed using the above described combination of sample dosing system, punching device and holder for the carrier matrix.

A further embodiment of the present invention includes sample dosing to be performed outside the punch/ sequencing block. In this case the individual samples are transferred with the sample dosing device (capillary system) onto the carrier matrix which is fixed by a holder.

In a preferred embodiment of the present invention, the base equipment of the device are advantageously five sequencing blocks (one of them is used as storage block for the samples), four lids, four holders for the carrier matrix, a sample dosing device and a punching device. All components of the system, especially the sequencing block, the sample dosing and punching device as well as the holders, are marked and thus can be combined in only one position, so that confusion of the samples are excluded.

During the performance of the solid phase sequencing process all essential operations are performed with or in the sequencing blocks (FIG. 4 operations 6, 9–19) without removing individual immobilized or eluted nucleic acid samples from the sequencing blocks. This is a further noticeable advantage which enables a considerable reduction of the analysis time, a high sample throughput and exclusion of sample confusion.

The use of the device system for solid phase sequencing of nucleic acid fragments described in the present invention allows simultaneous sequencing of many different nucleic acid fragments without confusing individual samples. The number of fragments which can be treated simultaneously depends only on the number of individual reaction vessels in the sequencing blocks (as well as on the sample dosing and punching device). The time for the sequence analysis can be considerably reduced and does not depend on the number of nucleic acid fragments to be analyzed.

DESCRIPTION OF A PREFERRED EMBODIMENT

Figure 1A:
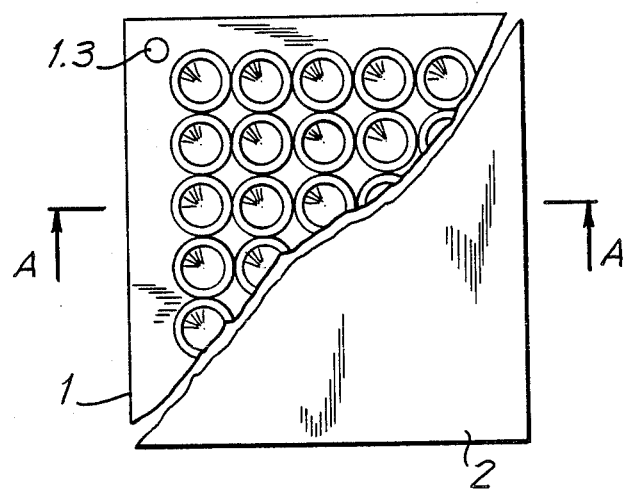
FIG. 1 sequencing block
a. semi-cut plan view with a lid
b. sectional view with lid
c. with deep drawing reaction vessels
FIG. 2
a. sample taking
b. sample dosaging
FIG. 3 sequencing block with punching device
FIG. 4 flow chart.

The base equipment of the device for performing the process of solid phase sequencing of nucleic acid fragments consists of five sequencing blocks (1), four lids (2), a sample dosing device (3), four holders for the carrier matrix (4) and a punch (5).

The sequencing block 1 (FIG. 1) is provided with a square like base block 1.1 made of high grade steel, wherein individual reaction vessels 1.2 (e.g. 0.1 ml, 0.5 ml or 1.5 ml plastic test tubes with a cylindrical shape or conical shaped form) or reaction vessels which are rigidly connected with each other in a microtiter plate manner 1.4 are inserted. Corners of the block are marked for unambigous orientation of the samples. One block is used for the storage of the samples to be sequenced. The other four sequencing blocks are additionally furnished with mechanical guides 1.3 (arrest) and thus can be combined unmistakably with the punch 5.

The lid 2 (FIG. 1b) fits precisely onto the sequencing block thereby closing each individual reaction vessel 1.2 or 1.4. It consists of a nondeformable rigid cover 2.2 and is additionally provided with a yieldable packing 2.1 which has plug like elevations 2.4. The block is sealed with the lid using special mounting elements 2.3 (e.g. screws and bores) situated on the corners.

The sample dosing device 3 (FIG. 2a) consists of the capillary holder 3.1 and the capillaries 3.2. The capillary holder, a rectangular plate corresponding to the shape of the sequencing block, has n bores corresponding to the number of individual reaction vessels in the sequencing block. The capillaries are inserted into the bores of the capillary holder, whereby the orifices 3.3 of the capillaries are disposed at one plane. The distance of the orifices to the capillary holder corresponds to the deepness of the reaction vessels. The diameter of the capillaries is somewhat smaller than the diameter of the punching pins 5.2 of the punch 5.

The holder for the carrier matrix 4 (FIG. 2b) is associated with a base plate 4.1 with a recess 4.2, a guide plate 4.3 and an arrest 4.5. Corresponding to the number and distribution of the reaction vessels the guide plate and the base plate are provided with bores 4.4 permitting the insertion of the capillaries and the punching pins 5.2. The diameter of the bores 4.4 should be smaller than the clear diameter of the reaction vessels 1.2.

The punching device 5 (FIG. 3) has the same rectangular shape as the sequencing block. It consists of a punching plate 5.1 in which punching pins 5.2 are inserted. The number and distribution of the punching pins correspond to the number and distribution of bores 4.4 in the holder 4 or reaction vessels 1.2 in the sequencing block. The diameter of the punching pins is so selected that they fit precisely into bores 4.4. The length of the punching pins corresponds at least to the thickness of the base plate 4.1 and the guide plate 4.3.

Figure 2A:
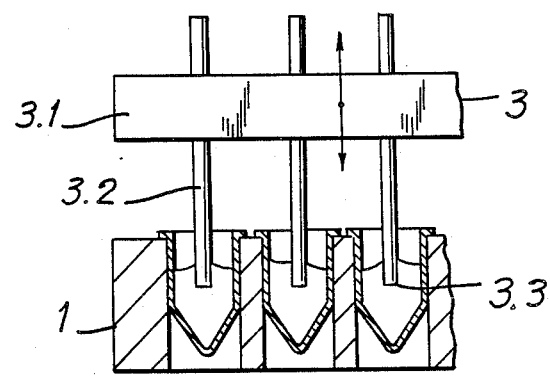
Figure 2B:
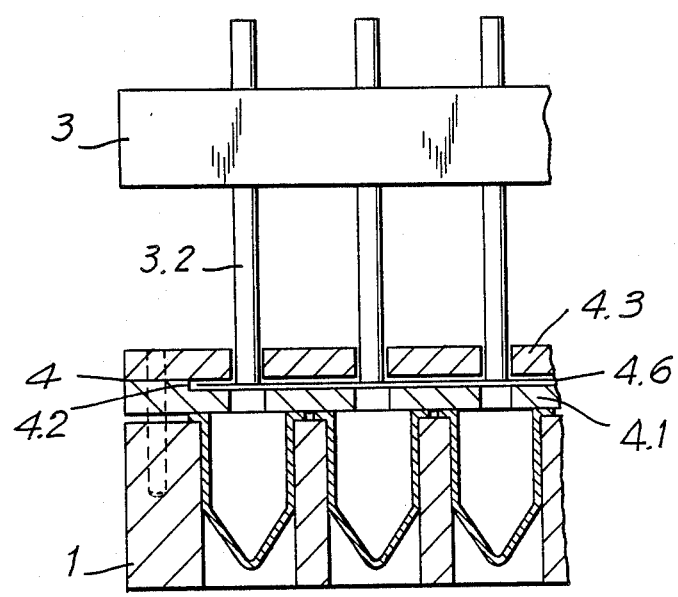
Figure 3:
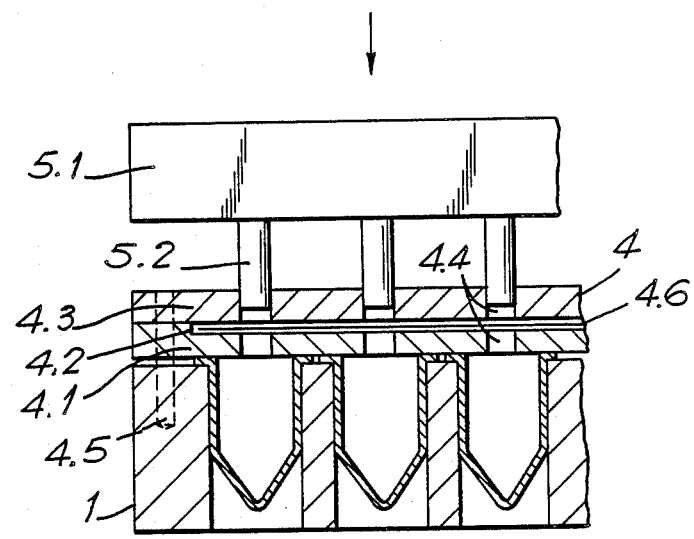
Figure 4:
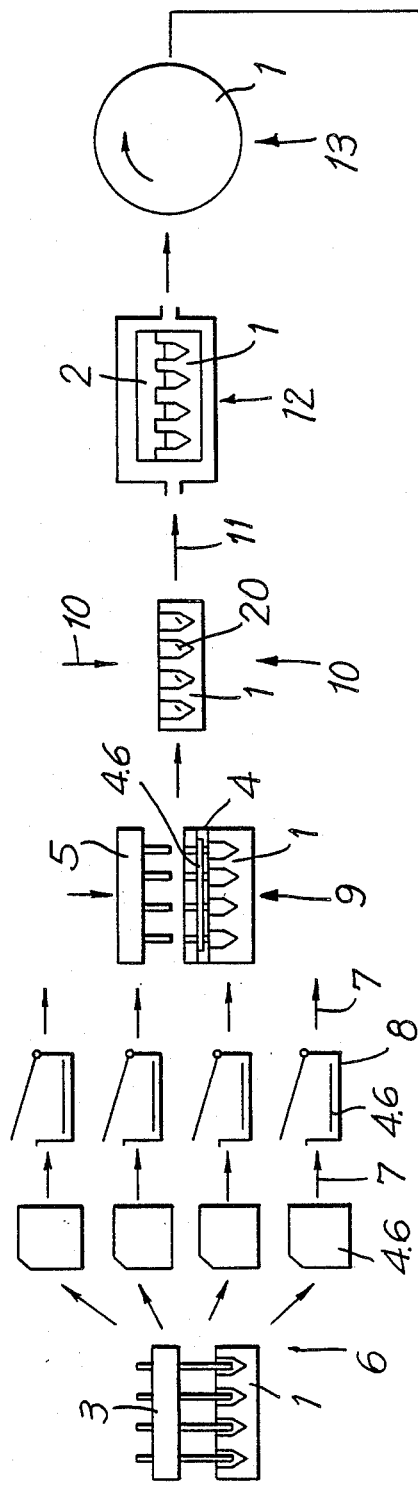
Figure 4:
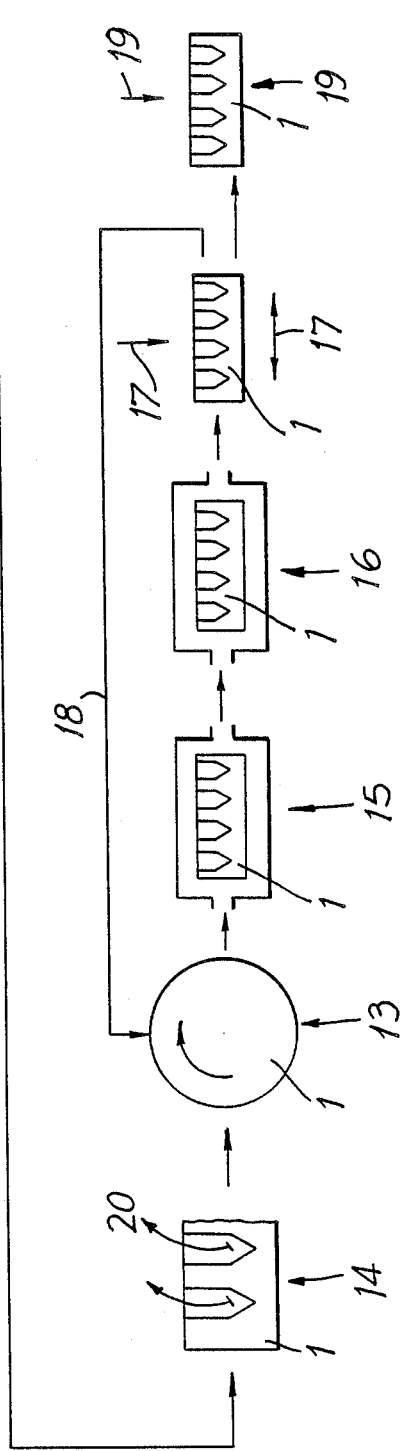

For performing the solid phase sequencing process of nucleic acid fragments (FIG. 4) the samples to be analyzed are filled into the reaction vessels 1.2 of one of the sequencing blocks 1 (storage block). The liquid samples are immobilized onto the carrier matrix by means of the sample dosing device 3. To achieve this, the capillaries are immersed into the acqueous solutions of the samples, whereby a somewhat uniform filling of the capillaries is obtained due to capillary forces (FIG. 2a). Subsequently, the sample dosing device is tightly pressed onto the carrier matrix 4.6 which is fixed in the recess 4.2 of base plate 4.1 of the holder 4 (FIG. 2b). During this operation the sample liquids are blotted and the nucleic acid fragments simultaneously fixed onto distinct areas of the carrier matrix. Thereby the carrier matrix receives a sample distribution pattern corresponding to the pattern of the reaction vessels in the sequencing block. The distance between the immobilized samples or the reaction vessels has to be selected in such a way as to avoid cross contamination of the radioactive labelled nucleic acid fragments. The immobilization procedure is repeated several times until at least four different carrier matrixes are loaded with the same set of samples. The loaded carrier matrices 4.6 are washed with water and ethanol (operation 7, FIG. 4), air dried and subsequently chemically treated by four different modification reactions (operation 8, FIG. 4). After removing the modification reagents by washing (operation 7, FIG. 4), the carrier matrix is inserted into the recess 4.2 of holder 4. The punching device 5 is combined with one of the four sequencing blocks 1, the punching pins 5.2 inserted into the bores 4.4 and n carrier segments containing the immobilized nucleic samples are punched out of each carrier matrix into the sequencing blocks (FIG. 3, FIG. 4, operation 9 and 10). This operation is repeated until all nucleic acid samples are punched out of the four carrier matrices into the four sequencing blocks. In case of DNA sequencing, aqueous piperidine is added to each reaction vessel of the sequencing blocks, the blocks sealed with the common lids 2, and heated to 90° C. for 30 min (FIG. 4, operation 12). As specified in the process for solid phase sequencing of nucleic acid fragment, during the piperidine reaction the DNA backbone is cleaved and the DNA fragments are chemically eluted off the carrier matrix. All further operations of the sequencing process like centrifuging, removing the carrier segments from the supernatans, lyophilizing the supernatants, cooling and shaking (FIG. 4, operation 12-18) are performed in or with the sequencing blocks. The sequence ladder of the nucleic acid sample is obtained by separation of the chemically degraded fragment by electrophoresis on denaturing polyacrylamide gels and autoradiography.

EXAMPLES

Example 1

Cellulose paper, for example, Whatman 540 paper is activated with cyanuric chloride in accordance with EP 134 025 and is immediately packaged. The paper (5 times 7) which had been surface treated in this manner is taken out of its special packing (welded foil, which is stored under $N_2$-gassing at $-20°$ C.) and is placed into a glass reaction chamber, wherein 2 mmol (450 mg) triethyl-1-amino-ethyl-ammonium-bromide in 7 ml acetoneitril were previously placed. The reaction chamber is shaken for about 12 hrs. at room temperature. After the completion of the reaction the paper is repeatedly washed with water and is dried between blotting paper. Instead of the solvent acetoneitrile watery buffer systems may be used.

Example 2

400 mg crystalline, nonderivitated cellulose an activation with cyanuric chloride is performed in accordance with EP 134 025 and subsequently reacted in a 25 ml round bottomed flask with 2 mmol (450 mg) triethyl-1-amino-ethyl-ammonium-bromide in 7 ml acetoneitril for 12 hours at room temperature. After the completion of the reaction the cellulose is washed repeatedly with water on a frit and is dried as in example 1.

Example 3

Cellulose (Whatman) 540 paper is surface activated with cyanuric chloride as in example 1 and subsequently placed into a glass reaction chamber, wherein previously 2 mmol (410 mg) 1-brome 2-amino-ethane-hydrobromide in 7 ml acetoneitril were placed. The reaction is then started by adding 5 ml triethyl amine. The reaction chamber is sealed with a parafilm and is shaken for about 12 hrs at room temperature. After the completion of the reaction the paper is washed and dried as in example 1.

Example 4

400 mg crystalline nonderivitized cellulose, for example, Whatman is activated with cyanuric chloride as in example 2 and is subsequently reacted in a 25 ml round bottom flask with 2 mmol (410 mg) 1-brome-2-amino-ethane-hydrobromide in 7 ml acetoneitril. The reaction is initiated by adding 5 ml triethyl amine and is completed after 12 hrs at room temperature by washing the cellulose and subsequent drying, as described in example 2.

Example 5

Surface activated Whatman 540 paper (5 times 7) from example 1 is reacted in a reaction chamber with 2 mmol (574 mg) p-amino-benzyl-triethyl-ammonium-bromide in 7 ml acetoneitril for 12 hrs. at room temperature and is further prepared as in example 1.

Example 6

400 mg crystalline surface activated Whatman cellulose in accordance with example 2 is reacted with 2 mmol (574 mg) p-amino-benzyl-triethyl-ammonium-bromide in 7 ml acetoneitril and further processed as described in example 2.

Example 7

Surface activated Whatman paper (5 times 7 cm) from example 1 is reacted with 2 mmol (54 mg) p-amino-benzyl-bromide hydrobromide in 7 ml acetoneitril in a reaction vessel and the reaction is initiated with 5 ml triethyl amine. After 12 hrs. at room temperature the paper is washed and dried as in example 1.

Example 8

400 mg crystalline surface treated Whatman cellulose in accordance with example 2 is reacted analog example 4 with 2 mmol (540 mg) p-amino-benzylbromide in acetonitrile and triethyl amine and is washed and dried after the completion of the reaction.

Example 9

Surface activated Whatman 540 paper (5 times 7 mm) from example 1 is reacted with 2 mmol Glycin-(o-nitromethyl-tri-ethyl-ammonium bromide)-benzylester in 7 ml acetoneitril for 12 hrs. at room temperature in a reaction chamber and further processed as in example 1.

Example 10

Semisynthetic paper of type Hekosyn ® (polyamide and cellulose) is surface activated with cyanuric chloride as in example 1 and subsequently placed into a glass reaction chamber wherein previously 2 mmol (410 mg) 1-bromo-2-aminoethane-hydrobromide in 7 ml acetoneitril were placed. The reaction is then initiated by adding 5 ml triethyl amine. The reaction chamber is sealed with parafilm and is shaken for about 12 hrs. at temperature. After completion of the reaction the paper is washed and dried as in example 1.

Example 11

Manually sequencing of individual oligonuclotide with chain lenght of 4 to 15 units 1. Radioactive labeling of the DNA-sequences 10–50 pmol oligonucleotide (or longer fragment) is labeled with the customary processes at the 5'-end with $^{32}P$-ATP and polynucleotide-kinase. After completing the kinase reaction the total volume is applied to a 20° polyacrylamide-gel, for example, which may contain urea (7 M), if need be, and is then separated gel-electrophoretically from ATP and other impurities like the undesirable side products. The desired DNA-band is made visible by a short autoradiography on X-ray film and is cut out from the gel. The gel piece is reduced to small pieces and transferred into an Eppendorf-Hütchen. The labeled oligonucleotide is recovered by two times extraction with water between 37° and 60° C. in 30 minutes.

2. Immobilization if the DNA-sequences on the face carrier with anion exchange characteristics 1–2 ul of the water solution obtained under 1 which contains, in addition to the labeled oligonucleotide, salt and urea, if need be, are applied dropwise on at least 4 about 2 mm times 2 mm large pieces of the face carrier (example 1–10). After a short drying of the paper pieces at room temperature or with heated air the operation of the dropwise application is continued until about 10 000 to 50 000 cpm per face carrier can be measured on a scintilation measuring device. The papers are subsequently washed in water and ethanol two times in succession with a tweezer (about 1 min.), and are dried between blotting paper by applying a pressure.

3. Chemical modification reactions for the oligonucleotide d(TCTA), d(TCTAGA), d(GTGAAUUCAC), d(TTCTTCTACACACCC) and d(TGATTCAGEGETGGCTTT) with a reaction surplus in the reaction vessel The 4 paper pieces obtained with immobilized labeled fragment of each oligonucleotide in accordance with 2 are placed individually in one each Eppendorf-Hütchen. The Eppendorf-Hütchen are marked in accordance with the modification reaction used. A total of 5 times 4=20 Eppendorf-Hütchen are present from the 5 oligonucleotides. The following reagents were added by pipettes:

G-reaction 200 ul cacodylate-buffer pH 8 or 200 ul ammonium formate-buffer pH 3.5

1 to 2 ul DMS

A+G-reaction 80 ul 88% formic acid

T C-reaction 80 ul of a $10^{-4}$ M KMnO$_4$-solution, which shortly before had been prepared from a $10^{-2}$ M of a stock solution C-reaction 40 ul of a 4 M hydroxyl amine solution pH 6 which was made from hydroxyl amine-hydrochloride by means of triethyl amine.

The reaction times for the G reaction 10 min. and for all other reactions 20 min. In addition to the mentioned reactions the T C-reaction may be reacted with osmium tetraoxide (80 ul of a 5 mM OsO$_4$-solution+1 ul pyridine. 15 min. at 0° C.), the AG-reaction with piperidine formate (80 ul piperidine formate pH 2.1 hr. at 37° C.) or diethyl pyrocarbonate (150 ul A-buffer (50 mM sodium acetate pH 5.+1 mM EDTA)+5 to 10 ul of a freshly made 10% DEPC-solution in ethanol, 20 min. at 90° C.). The T+C-reactions with hydrazine in accordance with Maxam and Gilbert or the A C-reaction with 1.2 M NaOH solution result in the complete loss of the radioactivity and can therefore not be used. During the aforementioned modification reaction the following losses occur: 20% in the G-reaction, 50% in the A+G-reaction, 0% in the T C-reaction and 50–80% in the C-reaction. These are balanced by the double or quadruple radioactivity in the A+G or in the C-reaction. The modification reactions are completed in the papers are removed from the reaction vessels by means of a tweezer and are successively washed two times with water and ethanol.

4. Piperidine-reaction for making the DNA-strand break and for simultaneous extraction of the fragments from the carrier The 20 paper carriers are placed invidivially into 20 new Eppendorf-Hütchen. After adding 50 ul of a 10% watery piperidine solution they are thermostated for 30 min. up to 90° C. After the completion of the reaction the papers are removed from the Eppendorf-Hütchen by means of a tweezer, the solutions are stored for 1 min. at −200° C., for example in liquid air and liophilized (for about 1 hr.). The liophisation step is repeated 2 times with 10 to 20 ul water (for about 30 min each). The samples are then ready for application on the gel electrophoresis.

Example 12

Simultaneous manual sequencing of large amounts of oligonucleotides with reagent surplus in the reaction vessel Labeling and immobilisation of 5 pentadecanucleotides d(TTCTTCTACACACCC), d(TGATCAGATGGCTTT), d(CTCCTGGCCATTCCT) d(GGGTACCCAGAAGTC) and d(TCGCTGAGATCACCA) is performed as described in example 11 (1. and 2.). The chemical modification reactions are now performed in only 4 Eppendorf-Hütchen, whereby 4 each paper carriers are contained therein. The reaction conditions and the subsequent washing operations are the same as in example 11 (3.). After washing and drying of the papers the previously identified carriers are again sorted out, so that again 4 individual papers are present per oligonucleotide, so that they can be individually placed into one each Eppendorf-Hütchen for the subsequent piperidine reaction. The piperidine reaction was performed analog to claim 11 (4.).

Example 13

Simultaneous manual sequencing of large amounts of oligonucleotides with reagent surplus in reaction vessels The labeling of the 5 pentadecanucleotide of example 12 is performed as described in example 11 (1.). The immobilisation of the fragments is not done this time on 4 times n (n=5) 20 (2 mm times 2 mm) large pieces of the face carrier, but on 4 (2 mm times 20 mm) large pieces in such a manner that about 1–2 ul of each oligonucleotides are placed dropwise on a face of 2 mm times 2 mm and that all oligonucleotides are placed onto the total face carrier. The 4 larger face carriers are subjected in larger reaction vessels (corresponding to the size of the face carriers to the already described modification reactions. After washing and drying of the carriers the 4 (2 mm times 20 mm) large face carriers are cut, with the assistance of a scissor, into 5 smaller (2 mm times 2 mm) large paper pieces and placed into 20 Eppendorf-Hütchen individually and subjected to the piperidine reaction. The piperidine reaction and the lyophilising is performed as already described.

Example 14

Manual sequencing of long DNA-sequences with reagent surplus in reaction vessels Long DNA-sequences are sequented completely analog as in examples 11, 12 and 13. Only the reaction times of the modification reactions listed in example 11 (3.) must be shortened to the following values: G-3 to 5 min. and all other reactions 10 min. The loss of radioactivity are substantially lower with the long DNA-fragments during the modification reactions.

Example 15

Manual sequencing of DNA-sequences without reaction surplus

The labeling and immobilisation of the DNA-sequences is performed analog to example 11 (1. and 2.) and 13. The face carriers are not placed into reaction vessels, like Eppendorf-Hütchen, but are placed onto a plane support covered with a plastic foil and is reacted with only that much volume of the modification reagents (example 11 (3.), that they are just wetted through. Generally, the volumes of 2 mm times 2 mm large papers are about 1–3 ul. If larger face carriers are used, for example, 2 mm times 20 mm, the volume of the reagents must be somewhat increased. All other operations like the duration of the modification reactions, washing and the piperidine reaction are performed as already described.

Example 16

Automatic performance of the process

A DNA/RNA-sequencing apparatus is constructed as follows. In the simplest case for sequencing of only one nucleic acid fragment, 4 thermostateable reactors equipped with a frit and a capacity of maximum 250 ul with a dosageable input and discharge are disposed parallel with respect to each other. The 4 individual face carriers (2 mm times 2 mm) with the immobilized labeled nucleic fragments are placed into the reactors. Now, the automatic operations in accordance with a predetermined program is performed: (1) washing; (2) chemical modification reactions; (3) washing; (4) piperidine-reaction (extraction). For this purpose the individual reagents are added by means of dosaging pumps in accordance with example 11 (3.) and remain in the reactor with a closed discharge valve for the time determined. After completion of the reactions the valves of the reactors are opened and the reagents discharge, if need be, under a slight air pressure. All washing steps with water and ethanol may be performed continously (with opened discharge valve the aforementioned reagents are alternately fed into the reactors) or discontinuously (100 ul volume of the aforementioned solvent are fed into the reactor, whereby the discharge valve is closed and remain there for a short time before they are again discharged). The carriers may be dried for a few seconds, if need be, with heated air at a discontinuous washing or at the end of the continuous washing process. For performing the piperidine reaction about 20–25 ul 10% of a watery piperidine solution is pumped into the 4 reactors (while the discharge valve is closed) and the reactor or the reactors are heated to 90° C. for 30 minutes. After opening the discharge valve the volumes of the piperine are blown into 4 individual Eppendorf-Hütchen under a slight air pressure which are connected by means of teflon hoses ($\phi$0.4–1 mm) with the reactors. The 4 Eppendorf-Hütchen with the extracted fragments are lyophilised either directly in the automat within a specific vacuum chamber or the liophilisation is performed outside of the system. In the first case the procedure is repeated after the first lyophisation with 10 to 20 ul water, which is automatically fed, and is repeated (2 or 3 times). The total time of the operation cycle takes about 2.5 hrs. In the second case with the manual lyophilisation the total time is about 20–30 min. The samples are then ready for the gel electrophoresis. In the more complicated case for sequencing large amounts of DNA-fragments the 4 reactors must have different spatial dimensions. The base face of a reactor with 8–15 fragments to be sequenced are about 0.5 cm times 6 cm. The 4 (0.4 cm times 5.5 cm) large face carriers with the applied 8–15 fragments are again placed into the reactors and the operations (1) and (2) are performed naturally with large volumes of reagents. After discharging the reagents of the modification reactions a washing (operation 3) is performed. Thereafter, the dried face carriers are automatically cut into smaller pieces by a defined realized technical principle and are simultaneously transferred into different piperine reactors provided with a frit and a discharge valve (about 50 reactors). This is performed by the construction of 4 movable modificationreactors, which lower by 180° after operation 3) and then open on the reactor lid. The face carriers are thereby brought into 4 movable (vertically displacement) cutting devices. Bu cutting off small pieces from the face carriers in the 4 vertically displaceable cutting devices the 4 times 8 to 15=32 to 45 piperidine reactors are charged with only 1 fragment in a controlled manner.

The piperidine reactions are performed analog, as already described. After completing the reaction the piperidine solutions with the extracted fragments transferred by means of a slight air pressure into the Eppendorf-Hütchen (about 50 pieces) which are connected with the reactors by means of teflon hoses and are subsequently lyophilised.

Example 17

Sequencing by use of high ion strengths for extracting the nucleic acid fragments from the carrier When using the described face carriers the extraction of the fragments before the piperidine reaction may also be performed with 1 to 2 M solutions of the salts of $NH_4HCO_3$, $(NH_4)_2CO_3$, $NH_4Ac$, $Et_3NHAc$, among others. The extraction is achieved in that the face carriers are individually reacted in reaction vessels, like the Eppendorf-Hütchen, two times with 50 ul of the aforementioned salt solutions at 60°. With the obligonucleotides the extractions are lyophilised, whereby the salts are evaporated during a repeated lyophilisation with watery ethanol. With long DNA-fragments the salts may be removed by means of ethanol-precipitation. Thereafter, the customary piperidine-reaction is performed in a homogenic phase.

Example 18

The basis equipment of the device for performing the solid phase sequencing consists of five sequencing blocks (1), four lids (2), a sample dosaging device (3), a puncher (5) and four face carrier holders (4). The sequencing block 1 is provided with a square like base block 1.1, wherein the reaction vessels 1.2 are inserted. The lid 2 fits precisely on the sequencing block. It is provided with a yieldable cover 2.1 which is mounted on the rigid cover 2.2, whereby the yieldable cover is provided with plug like elevations 2.4 corresponding to the number of the reaction vessels 1.2. The mounting elements 2.3 are mounted on the corners. These are usually two bars, which are being screwed into provided thread bores in the block. The face carrier holder 4 is associated with a base plate 4.1 with a recess 4.2, a guide plate 4.3 and the arrest 4.5. Corresponding to the number and the distribution sample of the reaction vessels 1.2 the guide plate and the base plates are provided with bores 4.4, which permit the the introduction of the punch pins 5.2 and the capillaries 3.2. The diameter of the bores 4.4 is smaller than the clear diameter of the reaction vessels 1.2.

The sample dosaging device consists of the capillary holder 3.1 and the capillaries 3.2. The capillary holder 3.1, a rectangular plate corresponding to the face of the sequencing block 1, has the same number of bores as the reaction vessels in the sequencing block. The capillaries 3.2 are displaceably introduced in the bores, whereby the orifices 3.3 of the capillaries are disposed at one plane and the distance of the orifices to the capillary holder is at least as large as the reaction vessels 1.2 are deep. The diameter of the capillaries 3.2 is somewhat smaller than the diameter of the bores 4.4 of the face carrier holder 4. The puncher 5 has the same rectangular shape as the sequencing block. It consists of a punch plate 5.1 and the punch pin 5.2 inserted therein, which in their number an in their distribution correspond to the number and the distribution of bores 4.4 in the face carrier holder. The diameter of the punch pins is so selected that they fit exactly into bores 4.4. The length of the punch pins 5.2 is at least as big as the base plate 4.1 and the thickness of the guide plate 4.3.

Figure 1B:
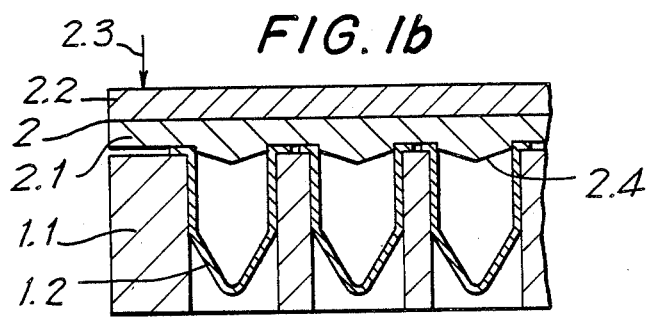
Figure 1C:
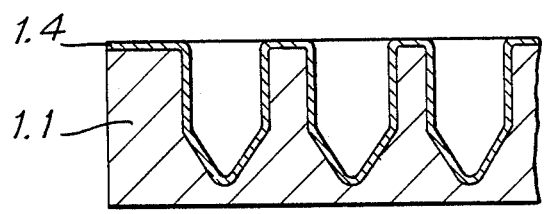

For performing the solid phase sequencing the samples to be stested are filled into the reaction vessels 1.2 of a sequencing block 1. With assistance of the sample dosaging device 3 a somewhat uniform filling of the capillaries are obtaine by immersing the capillaries into the watery solution and due to the active capillary forces (FIG. 2a). Subsequently the sample dosaging device is pressed onto the absorbable face absorption carrier 4.4 which is stationary disposed in the recess 4.2 of base plate 4.1. Thereby, the sample liquid is transferred to the carrier. The face carrier receives a sample pattern which corresponds to the pattern of the reaction vessel arrangement. The distance between the applied samples or between the reaction vessels is so selected that a flowing into each other is impossible (FIG. 1a). The same procedure is followed with three further face carriers, whereby the number of "inoculations" per face carrier is different in accordance with the aforementioned process, so that four "inoculated" face carriers are present after the completion of this process step which are now subjected to the known modification reactions. Thereafter, the face carrier is again inserted into the face carrier holder 4 into the provided recess 4.2. The puncher 5 with its punch pins 5.2 is inserted into the bores 4.4 and by pushing downwardly the sample containing area of the carrier are punched into the reaction vessels (FIG. 3). The same occurs with the further three inoculated carriers, so that four sequencing blocks with the immobilised samples are present in the reaction faces. Now, the addition of a piperidine solution into the reaction vessels of all sequencing blocks is performed as specified by the process, the lids 2 are inserted and all blocks are subjected to a simultaneous temperature treatment of 90° C. Thus a DNA-strand break occurs, while the extraction from the carrier is simultaneously performed. The further process steps, like shaking, separating the carrier fragments, centrifuging, cooling, lyophilising are performed in or with the sequencing blocks (see FIG. 4:13–19). The further processing of the samples for the purpose of separating and visualisation is performed by gel electrophoresis. A confusion of samples is excluded, since by placing of markings only one association of the elements of the device, like lid 2, sample dosaging device 3, face carrier holder 4 and puncher 5 is made possible with respect to the sequencing block. A further greater advantage is the simultaneous treatment of the face carrier elements 20 or the extracted samples until the point of application on the gel electrophoresis, without removing them from the sequencing block. Thereby, a considerable reduction of the analysis time is achieved as well as a high sample throughput in view of the selection of the number of the reaction vessels in the sequencing block.

It will be understood that each of the elements described above, or two or more together, may also find a useful application in other types of constructions differing from the types described above.

While the invention has been illustrated and described as embodied in a device for solid phase sequencing of nucleic acid fragments, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for solid phase sequencing of nucleic acid sequents comprising
    a plurality of sequencing blocks each storing and processing n nucleic acid fragments, said fragments being immoblized on individual carrier segments or in homogenous phase during a sequencing process, each of sequencing blocks including a base block and a plurality of reaction vessels inserted in said base block and corresponding to the number n of different nucleic acid fragments to be sequenced.
    a plurality of lids for closing said sequencing blocks each having a plug-like elevations according to a number and a distribution pattern of the reaction vessels;
    a sample dosing device for orienting n labeled nucelic acid samples from the sequencing blocks onto areas of a carrier matrix in a simultaneous fashion, said sample dosing device including a capillary holder and a plurality of capillaries with the number of the capillaries corresponding to the number n of different nucleic acid samples to be sequenced in each block, the capillaries being arranged in the capillary holder according to the distribution pattern of the reaction vessels and disposed on a flat plane with a distance between capillary orifices from the capillary holder greater than a depth of the reaction vessels;
    a plurality of carrier holders for fixing said carrier matrix in a predetermined position during the immobilization of the nucleic acid samples with the sample dosing device, each of the carrier holders having a recess with dimensions in height, width and depth corresponding to carrier holders also having a plurality of bores with a number and distribution pattern corresponding to those of the reaction vessels and with a diameter which is somewhat larger than a diameter of the capillary;
    a punch for simultaneous punching of n immobilized and chemically modified nucleic acid samples as said individual carrier segments out of the carrier matrix into the sequencing blocks, said punch including a punching plate and a plurality of punching pins corresponding to holes in the punch plate and arranged with a number and distribution pattern which also corresponds to those of the reaction vessels; and
    means for combining the sequencing blocks with the lids, the sample dosing device, the carrier holders and the punch, respectively.

2. Device for solid phase sequencing of nucleic acid fragments comprising:

a. five sequencing blocks each storaging and processing n nucleic acid fragments wherein n is defined as being between 1 and 1000, said fragments being immobilized on carrier segments or in a homogeneous phase during the sequencing process, each block incluidng a base block and reaction vessels which are inserted in the base block and correspond to the number n of different nucleic acid fragments to be sequenced;

b. four lids for closing said sequencing blocks, each including a nondeformable rigid cover and a yieldable packing with plug like elevations according to the number and the distribution pattern of said reaction vessels;

c. one sample dosing device for orienting the n labelled nucleic acid samples taken from one of said sequencing blocks onto distinct areas of a special carrier matrix in a simultaneous fashion, the sample dosing device consisting of a capillary holder and capillaries, whereby the number of said capillaries corresponds to the number n of different nucleic acid samples to be sequenced in each block, said capillaries are arranged to be inserted into said capillary holder according to the distribution pattern of said reaction vessels, and disposed on a flat plane with a distance between the capillary orifices from the said capillary holder being greater than the depth of said reaction vessels;

d. four carrier holders for fixing the special carrier matrix in a defined position during the immobilization of the nucleic acid samples with said sample dosing device, each carrier holder consisting of a base plate, with a recess which dimensions in height, width and depth correspond to the dimensions of the carrier matrix, a guide plate, whereby said base plate and said guide plate have exactly superimposed bores which number and distribution pattern corresponds to those of said reaction vessels and which diameter is somewhat larger than the diameter of said capillary;

e. a punch for simultaneous punching the n immobilized and chemically modified nucleic acid samples as individual carrier segments out of the carrier matrix into said sequencing blocks, said punch consisting of a punching 3. A device according to claim 2, wherein the reaction vessels inserted into the sequencing blocks have a cylindrical shape.

4. A device according to claim 2, wherein the reaction vessels inserted into the sequencing blocks have a conical shape.

5. A device according to claim 2, wherein the reaction vessels comprise test tubes of 30 $\mu$l to 2 ml.

6. A device according to claim 2, wherein the reaction vessels comprise tubes which are rigidly connected in a microliter plate manner.

7. A device according to claim 2, wherein the reaction vessels comprise tubes which are formed as deep-drawn members from a foil.

8. A device according to claim 2, wherein the reaction vessels comprise individual deep-drawn tubes which are connected with one another and easily insertable into the sequencing block and replaceable.

9. A device according to claim 2, wherein the sequencing blocks are made from such a material which exhibit sufficient heat conducting properties and allow the reaction vessels to be easily heated to over 90° C.

10. A device according to claim 2, wherein the capillaries have an inner diameter between 0.1 and 3 mm.

11. A device according to claim 2, wherein the sample dosing device is formed so that it is capable to transfer n different nucleic acid fragments from the sequencing blocks to the carrier matrix, whereby each transferred sample has a volume between 0.5 and 5 $\mu$l.

12. A device according to claim 2, wherein the punching device is formed so that it is capable to punch out n disc shaped segments out of the carrier matrix in a simultaneous fashion, so that each segment has a diameter within the range of 0.5 to 5 mm.

* * * * *